US010888215B1

(12) United States Patent
Doukides

(10) Patent No.: US 10,888,215 B1
(45) Date of Patent: Jan. 12, 2021

(54) FLUID COLLECTION VESSEL FOR USE WITH AN ENDOSCOPE

(71) Applicant: Theodore Pano Doukides, Boca Raton, FL (US)

(72) Inventor: Theodore Pano Doukides, Boca Raton, FL (US)

(*) Notice: Subject to any disclaimer, the term of this patent is extended or adjusted under 35 U.S.C. 154(b) by 0 days.

(21) Appl. No.: 16/541,725

(22) Filed: Aug. 15, 2019

(51) Int. Cl.
| | | |
|---|---|---|
| A61B 1/00 | (2006.01) | |
| A61B 1/012 | (2006.01) | |
| A61B 90/00 | (2016.01) | |
| B67C 11/00 | (2006.01) | |
| B67C 11/02 | (2006.01) | |
| A61B 90/40 | (2016.01) | |

(52) U.S. Cl.
CPC .......... *A61B 1/00137* (2013.01); *A61B 1/012* (2013.01); *A61B 90/05* (2016.02); *B67C 11/00* (2013.01); *B67C 11/02* (2013.01); *A61B 90/40* (2016.02)

(58) Field of Classification Search
CPC ..... A61B 1/00137; A61B 1/012; A61B 90/05; A61B 90/40; A61J 1/05; A61J 1/1462; A61J 1/1481; B67C 11/00; B67C 11/02
USPC ................. 137/312–314; 220/4.26, 23.4; 141/331–332
See application file for complete search history.

(56) References Cited

U.S. PATENT DOCUMENTS

| | | | | | |
|---|---|---|---|---|---|
| 34,004 | A | * | 12/1861 | Morrison ................ | B67C 11/02 141/343 |
| 474,036 | A | * | 5/1892 | Wood ..................... | B67C 11/02 141/340 |
| 949,074 | A | * | 2/1910 | Hickox ................... | B65D 1/02 141/343 |
| 1,733,261 | A | * | 10/1929 | Higby .................... | B67C 11/02 141/337 |
| 1,935,324 | A | * | 11/1933 | Lillard ................... | B67C 11/02 141/337 |
| 5,308,318 | A | | 5/1994 | Plassche, Jr. et al. | |
| 5,403,277 | A | | 4/1995 | Dodge et al. | |
| 6,626,827 | B1 | | 9/2003 | Felix et al. | |
| 7,220,227 | B2 | | 5/2007 | Sasaki et al. | |
| 7,976,533 | B2 | | 7/2011 | Larsson | |
| 9,215,964 | B2 | | 12/2015 | Loske | |
| 9,713,461 | B2 | | 7/2017 | Mikkaichi et al. | |
| 2006/0195117 | A1 | | 8/2006 | Rucker et al. | |
| 2007/0142702 | A1 | | 6/2007 | Haller et al. | |

(Continued)

OTHER PUBLICATIONS

Non-Final Office Action dated Apr. 17, 2012 for U.S. Appl. No. 12/467,726, pp. 1-9.

*Primary Examiner* — Aaron B Fairchild
(74) *Attorney, Agent, or Firm* — The Concept Law Group, PA; Scott D. Smiley; Scott M. Garrett

(57) ABSTRACT

A fluid collection vessel includes a catch portion that is configured to attach to an endoscope adjacent the port. The catch portion directs any leaked fluids the come out of the port into a neck portion that leads to a collection chamber. The catch portion includes an indented portion that is shaped and sized in correspondence with the neck and body of the endoscope so as to locate the port over the approximate center of the opening of the catch portion. The neck portion is an elongated component having a relatively narrow cross section that tends to inhibit spillage in the event of the collection vessel falling or being laid on its side.

11 Claims, 13 Drawing Sheets

(56) References Cited

U.S. PATENT DOCUMENTS

2009/0287111 A1  11/2009  Kaye et al.
2015/0291408 A1* 10/2015  Fox .................. B60K 15/03504
                                                141/1

* cited by examiner

FLUID COLLECTION VESSEL FOR USE WITH AN ENDOSCOPE

FIELD OF THE INVENTION

The present invention relates generally to accessories for endoscopes, and more particularly to a collection vessel for collecting fluids leaking out of the endoscope during use.

BACKGROUND OF THE INVENTION

Endoscopic retrograde cholangiopancreatography (ERCP) is procedure in widespread use by physicians, and is used to diagnose conditions of a patient's liver, gallbladder, bile ducts, and pancreas. Using ECRP a physician can diagnose and treat conditions of the bile ducts, including gallstones, scars, leaks, and cancer. In the practice of ERCP, the endoscope's optical features can be used to see inside a patient's stomach and duodenum, and other portions of the gastrointestinal tract. X-rays can be used in conjunction with dyes released or injected by the endoscope into ducts, the biliary tree, and the pancreas in order to see features and conditions of those structures.

In some uses of an endoscope, the endoscope is inserted into the upper gastrointestinal tract though the patient's mouth, down the esophagus and stomach, and into the duodenum where the bile duct is located. The endoscope includes a tube for an instrument channel through which articles can be passed an introduced into the patient. The tube is accessed through a port at a proximate end of the endoscope, the port typically being located on a neck that extends outward from a main body portion of the endoscope. The port is oriented to facilitate entry into to tube. A guide wire is commonly inserted through the tube to allow the physician to place a catheter or other articles into the bile duct. As a result, bile will often be forced up the instrument channel of the endoscope, and out of the port, leaking onto the floor of the examining room, if not onto the physician and other objects in the examining room.

The problem of bile and other bodily fluids leaking out of an endoscope during examination is well known, and solutions for this problem have been tried. One of the more common approaches to dealing with the leakage is to place a collection device around the port on the endoscope that is rigidly mounted to the endoscope. However this approach does not contain the collected fluids well, and tipping the endoscope can result in the collected fluid spilling or leaking out of the collection device due to the wide opening and relatively short distance to bottom of the collection device.

Therefore, a need exists to overcome the problems with the prior art as discussed above.

SUMMARY OF THE INVENTION

In accordance with some embodiments of the inventive disclosure, there is provided a collection vessel for use with an endoscope which has a main body portion with a neck extending from the main body portion, and a port at a top of the neck. The collection vessel includes a catch portion configured to be positioned under the neck of the endoscope, and the catch portion has an open top defined by a rim and a wall extending downward and inward from the rim to a bottom opening of the catch portion. The collection vessel further includes a neck portion joined at a top of the neck portion to the bottom of the catch portion at the bottom opening of the catch portion. The neck extends downward from the bottom of the catch portion and having a bore through the neck portion to a bottom of the neck portion. The collection vessel further includes a collection chamber joined to the bottom of the neck portion defining a collection volume within a wall of the collection chamber, wherein the wall of the collection chamber extends outward from the bottom of the neck portion.

In accordance with a further feature, the top of the neck portion and the bottom of the catch portion are threaded to join together, and the bottom of the neck portion is threaded to join to the collection chamber.

In accordance with a further feature, the catch portion is conically shaped.

In accordance with a further feature, the catch portion has a front that includes an indented portion that is configured to fit over the neck and a portion of the main body portion of the endoscope.

In accordance with a further feature, a wire lock portion extends upward from a side of the indented portion and is configured to be adjacent the port at the top of the neck of the endoscope.

In accordance with a further feature, the neck portion is cylindrical, having circular cross section.

In accordance with a further feature, the neck portion further includes, in the bore of the neck portion, at least one downward angled backflow prevention wall that extends from one side of the bore across a central axis of the bore to a free end of the at least one downward angled backflow prevention wall, and wherein there is a gap between the free end and an opposite side of the bore.

In accordance with a further feature, the at least one downward angled backflow prevention wall is a first downward angled backflow prevention wall, the neck portion further includes a second downward angled backflow prevention wall below the first downward angled backflow prevention wall, wherein the second downward angled backflow prevention wall is oriented in an opposite direction from that of the first downward angled backflow prevention wall.

In accordance with a further feature, the collection vessel include a strap coupled to the collection vessel at a first side at one of either the catch portion or the neck portion, and wherein the strap is configured to secure the collection vessel to the endoscope by wrapping around the main body portion of the endoscope to a second side of the collection vessel.

In accordance with a further feature, the collection chamber has a flat bottom.

In accordance with some embodiments of the inventive disclosure, there is provided a collection vessel for use with an endoscope. The endoscope having a main body portion, and the main body portion of the endoscope having a neck extending from the main body portion, and a port is located at a top of the neck. The collection vessel includes a catch portion having an inverted conic shape that is open at a top of the catch portion and that defines a rim that is substantially circular. The catch portion further includes a wall extending downward and inward from the rim to a bottom of the catch portion, which includes a bottom opening. An indented portion is formed in the wall from the rim that is shaped to correspond to the neck of the endoscope, and the indented portion is shaped such that when the indented portion is positioned over the neck of the endoscope, the port on the neck of the endoscope is substantially centered over the top of the catch portion. The collection vessel further includes a neck portion joined at a top of the neck portion to the bottom of the catch portion at the bottom opening of the catch portion. The neck portion extends downward from the bottom of the catch portion and has a bore through the neck portion to a bottom of the neck portion. The collection vessel further includes a collection chamber joined to the bottom of the neck portion defining a collection volume within a wall of the collection chamber, wherein the wall of the collection chamber extends outward from the bottom of the neck portion. The neck portion further includes at least one backflow prevention feature disposed in the bore of the neck portion that is configured to inhibit a flow of fluid toward the catch portion and to facilitate flow of fluid in a direction toward the collection chamber.

In accordance with a further feature, the top of the neck portion and the bottom of the catch portion are threaded to join together, and the bottom of the neck portion is threaded to join to the collection chamber.

In accordance with a further feature, the catch portion includes a threaded extension at the bottom of the catch portion that is configured to thread into the top of the neck portion, and the bottom of the neck portion includes a threaded extension that is configure to thread into the top of the collection chamber.

In accordance with a further feature, a wire lock portion extends upward from a side of the indented portion and is configured to be adjacent the port at the top of the neck of the endoscope.

In accordance with a further feature, the neck portion is cylindrical, having circular cross section.

In accordance with a further feature, the at least one backflow prevention feature includes at least one downward angled backflow prevention wall that extends from one side of the bore across a central axis of the bore to a free end of the at least one downward angled backflow prevention wall, and wherein there is a gap between the free end and an opposite side of the bore.

In accordance with a further feature, the at least one downward angled backflow prevention wall is a first downward angled backflow prevention wall, the neck portion further includes a second downward angled backflow prevention wall below the first downward angled backflow prevention wall, wherein the second downward angled backflow prevention wall is oriented in an opposite direction from that of the first downward angled backflow prevention wall.

In accordance with a further feature, the collection vessel further includes a pair of strap retention features formed on an outside of the wall of the catch portion, with one strap retention feature being disposed on a first side of the indented portion and one strap retention feature being disposed on a second side of the indented portion opposite the first side of the indented portion.

In accordance with a further feature, the collection chamber has a flat bottom.

In accordance with a further feature, the neck portion is at least in part collapsible, having at least one accordion section.

Although the invention is illustrated and described herein as embodied in a collection vessel for use with an endoscope, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the length of the collection vessel. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
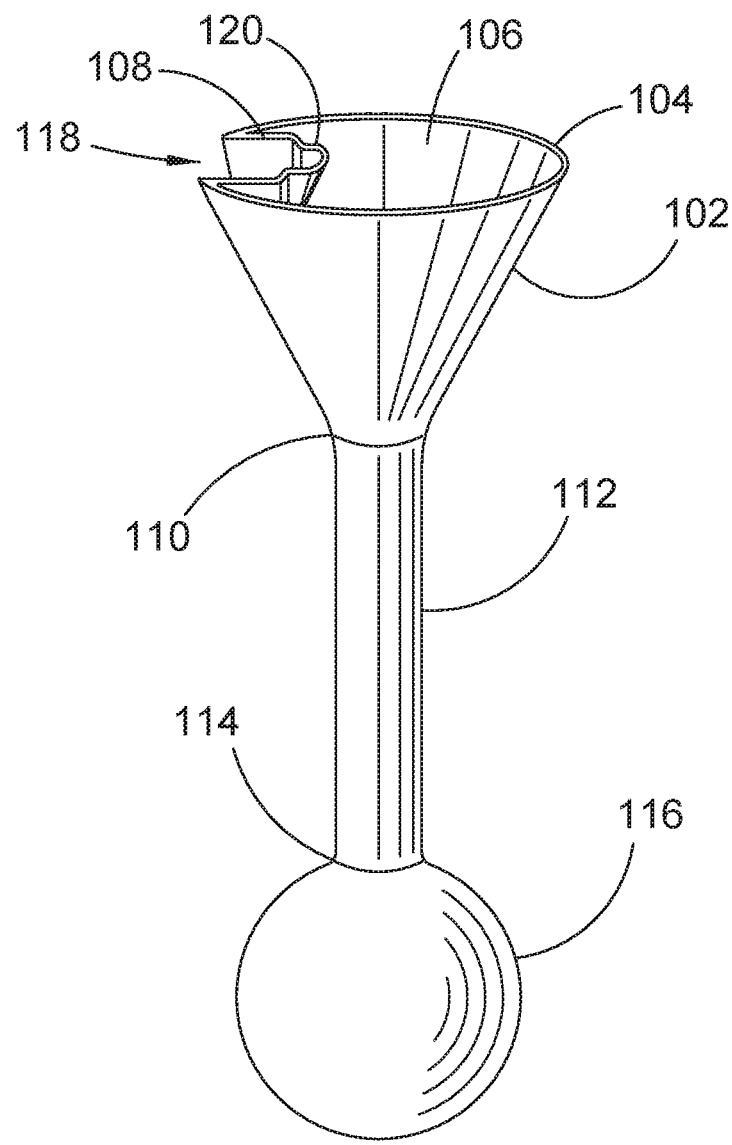
FIG. 1 is a perspective view of a collection vessel for use with an endoscope, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

FIG. 1 is a perspective view of a collection vessel 100 for use with an endoscope, in accordance with some embodiments. The collection vessel 100 is configured to be used with an endoscope to collect bile and other bodily fluids that escape through the port of the endoscope. The collection vessel 100 is configured to be used with an endoscope by having a portion of the collection vessel 100 is shaped and contoured to provide an interface with the endoscope and help hold the collection vessel 100 in place while being used with the endoscope. The collection vessel 100 has three major portions; a catch portion 102, a neck portion 112, and a collection chamber 116. The catch portion 102 is configured to catch fluids leaking through the port of the endoscope and direct them into the neck portion 112. The neck portion 112 is a conduit to the collection chamber 116 and at a minimum creates a distance between the catch portion 102 and the collection chamber 116 to facilitate the trapping of fluids away from the catch portion 102. The collection chamber 116 is configured to hold collected fluids during usage of the endoscope, and for disposal. In some embodiments the collection vessel 100 is a unitary article with the various portions formed together as one unit. In some embodiments the various portions of the collection vessel 100 are formed separately and assembled for use by pre-designed interconnection features.

The catch portion 102 is a generally conic section having up upper rim 104 defining an opening 106. In order to fit with an endoscope, and indented portion 108 is formed to receive a portion of an endoscope, and the indented portion 108 is formed to follow the profile or shape of a portion of an endoscope, particularly at the neck of the endoscope where the port is located, since bodily fluids leak out of the port. The catch portion 102 is, more specifically, and inverted conic shape with a sidewall that goes from the rim 104 downward and inward at the bottom 110 of the catch portion, which is also the top of the neck portion 112. The opening 106 of the catch portion can be generally circular, although other shapes can be used. Circular can be preferred in order to avoid having corners that may catch on garments or poke the user of the endoscope during use.

In indented portion 108 is configured to fit around a particular location on the endoscope, specifically over the neck and main body section of the endoscope. The neck of the endoscope fits into a sloping section 120 and the main body of the endoscope can fit into the wider section 118. The indented portion 108 is configured to allow the opening 106 to substantially surround the port of the endoscope, as will be shown, in order to minimize the chance of fluids leaking out of the port avoiding the collection vessel. That is, by providing the indented portion 108 in the side wall of the catch portion 102, the center of the opening 106 can be located under the port of the endoscope, thereby maximizing the area of the opening 106 that surrounds the port of the endoscope. The opening 106 can have a dimension of two inches to four inches, from one side to the opposite side, in some embodiments. The height of the catch portion, vertically from the bottom 110 to the rim 104 can likewise be on the order of two to four inches tall. The sidewall of the catch portion can be straight as shown, or have some curvature.

The neck portion 112 has a substantially reduced cross section diameter or area compared to the area or diameter of the opening 106 of the catch portion 102. In some embodiments the neck portion 112 can have a circular horizontal cross section (horizontal to the page, as drawn in FIG. 1), and have a diameter of one quarter of an inch to one inch. The distance from the top 110 to the bottom 114 can be on the order of two to six inches in some embodiments, more or less in other embodiments. The purpose of the neck portion is two-fold; first, the narrower passage is forms can be restrictive to backflow in the event the collection vessel 100 is inadvertently upended, or dropped. Secondly, it lowers the position of the collected fluids, thereby shifting the weight of the collected fluid away from the main body of the endoscope resulting in a different weight distribution than when the fluids are collected around the port of the endoscope. It also provides a measure of assurance to the operator of the endoscope that collected fluids aren't likely to spill or be otherwise accessible as with some prior art approaches that use wide openings and simply hold the collected fluids proximate to the endoscope port. To further reduce the possibility of backflow, the neck portion 112 can contain structures inside the passageway of the neck portion 112 that obstruct the flow of fluids in one direction. After passing through the neck portion 112, collected fluids will fall into the collection chamber 116. The collection chamber 116 can be spherical, or partially spherical in some embodiments, and other shapes in some other embodiments. The collection chamber 116 is where the collected fluids are ultimately held in side a collection volume of the collection chamber, and the shape of the collection chamber is such that it can contain fluids and prevent them from flowing back up the neck portion 112 even if the collection vessel is laid horizontally. This is accomplished by having the wall of the collection chamber 116 extend outward from the bottom 114 of the neck portion 112, as well as the outward extent of the rim 104 of the catch portion 102.

Figure 2:
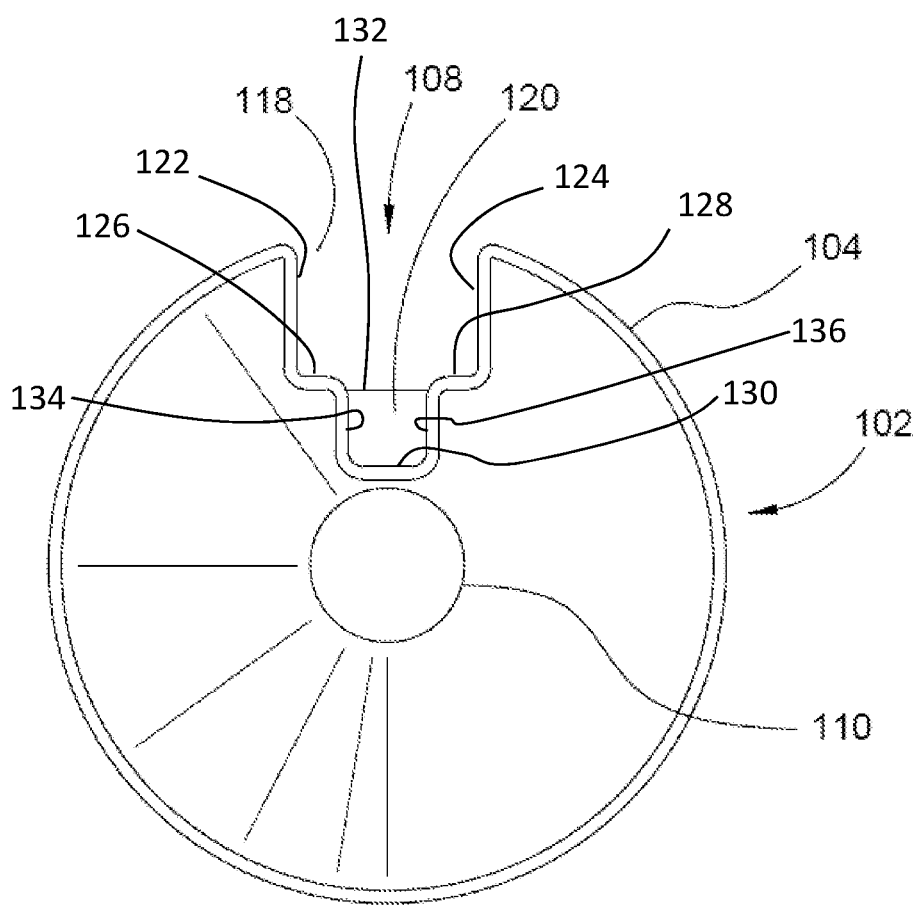
FIG. 2 is a top plan view of an upper portion of a collection vessel for use with an endoscope, in accordance with some embodiments.

FIG. 2 is a top plan view of an upper portion of a collection vessel 100 for use with an endoscope, in accordance with some embodiments. In particular the rim 104 of the catch portion 102 is shown with a substantially circular shape. In the center, and below the level of the rim 104 (i.e. into the page) is the opening into the top 110 of the beck portion. The indented portion 108 is formed and sized to receive a portion of an endoscope referred to as the neck, on which is a port for inserting instrument and articles into the endoscope during use. The sloping section 120 is sized specifically to receive the neck of the endoscope on which the port is located, and the wide section 118 is sized to receive a body portion of the endoscope from which the neck extends. As used here, the term "sized to receive" means the structure is shaped and dimensioned correspondingly to the shape and dimension of the structure intended to fit therein, leaving minimal gap that allows a user to place the structures together and take them apart, but without such spacing that allows undue shifting of the structures relative to each other. The wide section 118 is defined by opposing outer wall sections 122, 124 that extend inward from the outside of the catch portion, and parallel to each other, to shoulder portions 126, 128. The shoulder portions 126, 128 extend toward each other from the outer wall sections 122, 124 to inner wall sections 134, 136, respectively. The inner wall sections 134, 136 extend inward further from the shoulder portions 126, 128 to a back section 130 of the sloping portion 120. The sloping portion 120 slopes outward from the top of the back section 130 to a bottom 132 at the shoulder portions 126, 128. The distance between the outer wall sections 122, 124 is greater than a distance between the inner wall sections 134, 136.

Figure 3:
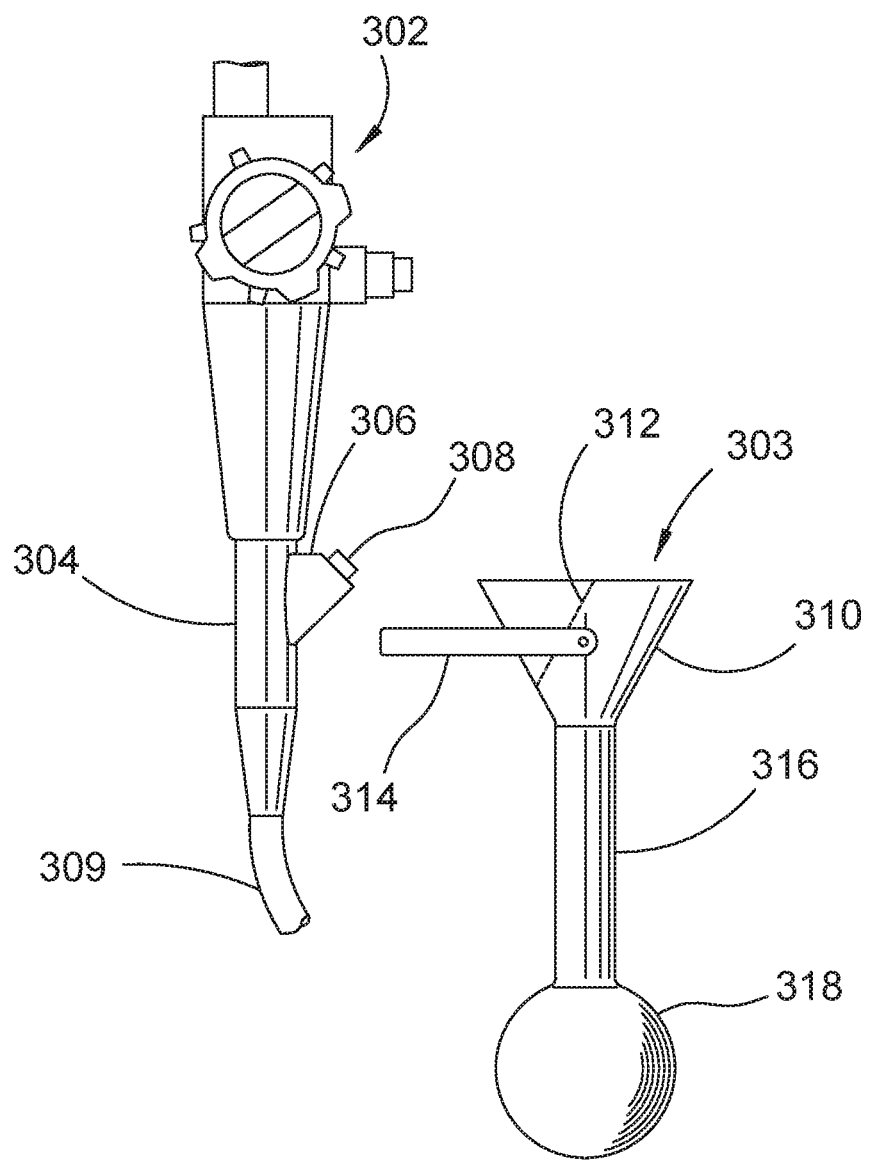
FIG. 3 is a side view of an endoscope and a collection vessel for use with the endoscope, with the collection vessel not attached to the endoscope, in accordance with some embodiments.
Figure 4:
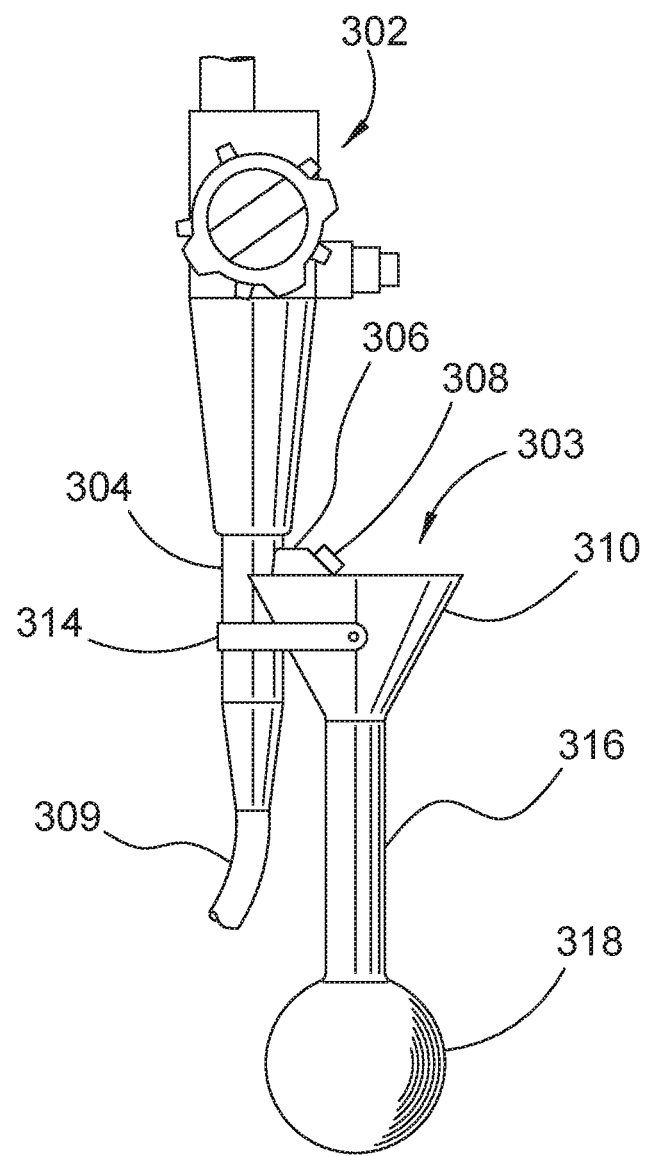
FIG. 4 is a side view of an endoscope and a collection vessel for use with the endoscope, with the collection vessel attached to the endoscope, in accordance with some embodiments.

FIG. 3 is a side view 300 of an endoscope 302 and a collection vessel 303 for use with the endoscope 302, with the collection vessel 303 not attached to the endoscope 302, in accordance with some embodiments. FIG. 4 shows the collection vessel 303 joined to the endoscope 302. The endoscope 302 includes a main body portion 304 from which a neck 306 extends, having an angled or sloping profile. On an angled top portion of the neck 306 is a port 308 that allows access to the main body portion 304 and the tube or channel 309. The port 308 is used, for example, by the operating physician to insert guide wires and articles such as stents.

The collection vessel 303 includes a catch portion 310 that has an indented portion 312 that is configured to receive the neck 306 and part of the main body portion 304, and is shaped and dimensioned in correspondence with the external shape of the neck 306 and main body portion 304. The indented portion can be configured to allow the port 308 to be substantially centered over the catch portion 310. The collection vessel 303 also includes a neck portion 316 and a collection chamber 318. The catch portion 310 can be generally conic (inverted), having a wide opening that is proximate to the port 308 when the collection vessel is attached to the endoscope 302. The narrower bottom of the catch portion 310 joins to the top of the neck portion 316, and the bottom of the neck portion 316 joins with the top of the collection chamber 318. A strap 314 can be used to further secure the collection vessel 303 to the endoscope 302 at the main body portion 304. The strap 314 is coupled to the catch portion 310 on one side of the indented portion 312, and goes around/behind the main body portion 304 of the endoscope 302 to connect back to the catch portion 310 on the other side of the indented portion 312. Strap retention features on either side of the catch portion, or on either side of the indented portion, are configured to interface with, and retain the strap 314. Once the collection vessel 303 is attached to the endoscope 302, as in FIG. 4, the endoscope 302 can be used normally, and any fluids that exit the port 308 will fall into the collection vessel 303 and be retained in the collection chamber 318 for subsequent disposal.

Figure 5:
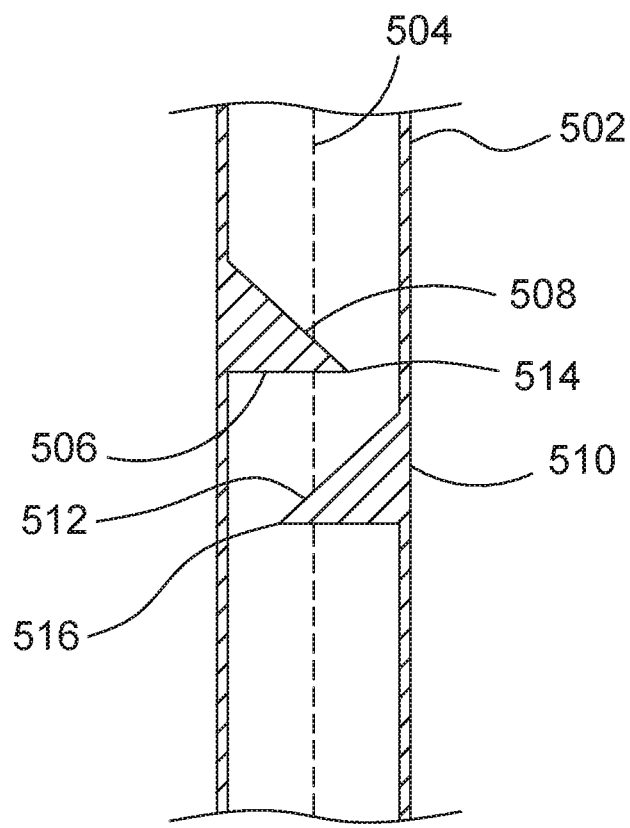
FIG. 5 is a vertical cross section view from the side of a neck portion of a collection vessel having backflow prevention walls, in accordance with some embodiments.

FIG. 5 is a vertical cross section view 500 from the side of a neck portion 502 of a collection vessel having backflow prevention walls, in accordance with some embodiments. The neck portion 502 is elongated and narrowed so that the resulting geometry of the collection vessel, particularly the catch portion and collection chamber, tend to prevent the collection vessel tilting such that fluids collected in the collection chamber are retained even when the collection vessel is on its side. However, to further ensure that fluids do not unintentionally escape from the collection vessel, the neck portion 502 can include one or more backflow prevention features or walls 508, 510. The backflow prevention walls 508, 510 are structures formed in the bore of the neck portion 502 that form barriers which tend to prevent fluids from exiting the collection vessel, while allowing fluids to pass into the collection chamber with minimal obstruction. The tops of each of the backflow prevention walls 508, 510, like top surface 512 of backflow prevention wall 510, is sloped from wherein joins the inside surface of the neck portion 502 downward to a free edge 514, 516. The undersides, such as underside 506 of the backflow prevention wall 508, can be sloped like the top surface, or at some other angle to a flat (e.g. horizontal) configuration. The underside of each backflow prevention wall 508, 510 acts as an obstruction if the collection vessel is tilted from its vertical orientation during normal usage, or if the collection vessel is impacted, which could otherwise splash collected fluids up the neck portion. The free ends 514, 516 of the backflow prevention walls 508, 510 can extend across a center bore line 504 through the center of the bore of the neck portion 502 so that, when there is more than one of the backflow prevention walls 508, 510 the free ends 514, 516 overlap, vertically.

Figure 6:
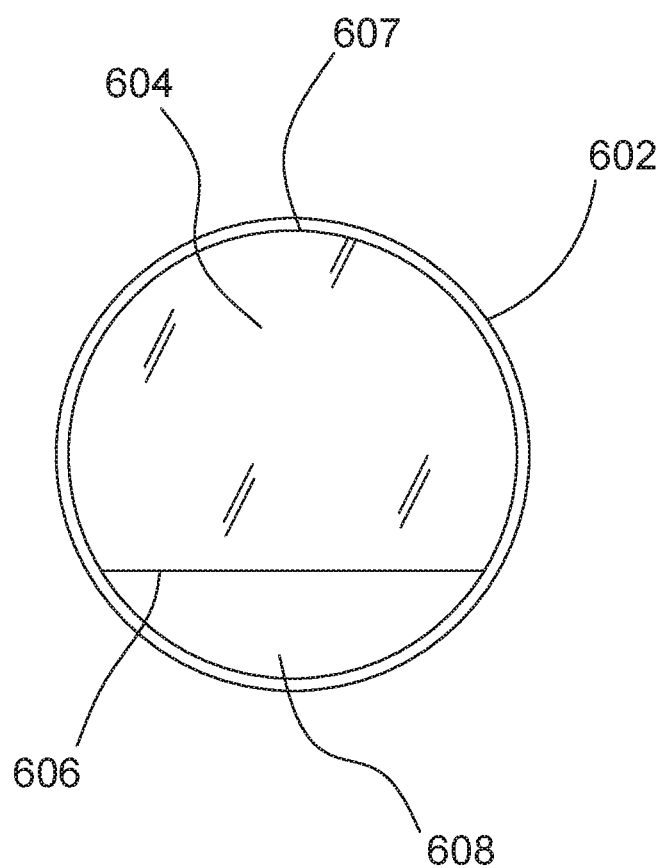
FIG. 6 is a horizontal cross section view from the top of a neck portion of a collection vessel having backflow prevention walls, in accordance with some embodiments.

FIG. 6 is a horizontal cross section view 600 from the top of a neck portion of a collection vessel having backflow prevention walls, in accordance with some embodiments. The view 600 can be of neck portion 602 that is substantially similar, if not identical, to that shown in FIG. 5. Looking down into the central axis of the bore of the neck portion, the top surface 604 of a backflow prevention wall can be seen. The top surface is sloped such that the free end 606 is lower than the top end 607. A gap 608 results between the free end 606 of the backflow prevention wall and the inside surface of the neck portion 602. Fluids entering the neck portion pass through the gap 608 and then pass into the collection chamber below. The backflow prevention wall thereby facilitates the collection of fluids in the collection chamber, and provides an obstacle to fluids that may travel in the opposite direction if the collection vessel is impacted (splash), such if it falls onto the floor, or if the collection vessel is laid horizontally, giving the user time to right the collection vessel before more of the fluid can spill out.

Figure 7:
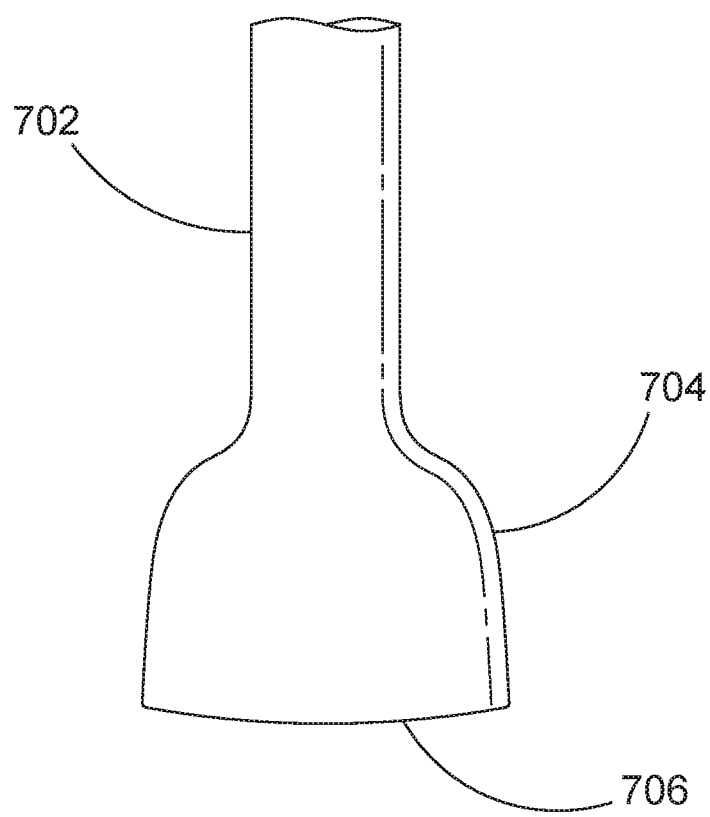
FIG. 7 is a side plan view of a collection chamber of a collection vessel for use with an endoscope and having a flat bottom, in accordance with some embodiments.

FIG. 7 is a side plan view of a collection chamber 704 of a collection vessel 700 for use with an endoscope and having a flat bottom 706, in accordance with some embodiments. The neck portion 702 joins with the top of the collection chamber 704 as previously described, but instead of a spherical collection chamber, the collection chamber 704 has a flat bottom 706, specifically meaning at a perpendicular angle to the bore of the neck portion 702. This allows the collection vessel 700 to be stood upright on a level surface. Similarly, the collection chamber 704 can have a vertically flattened side to prevent the collection vessel from rolling on a surface.

Figure 8:
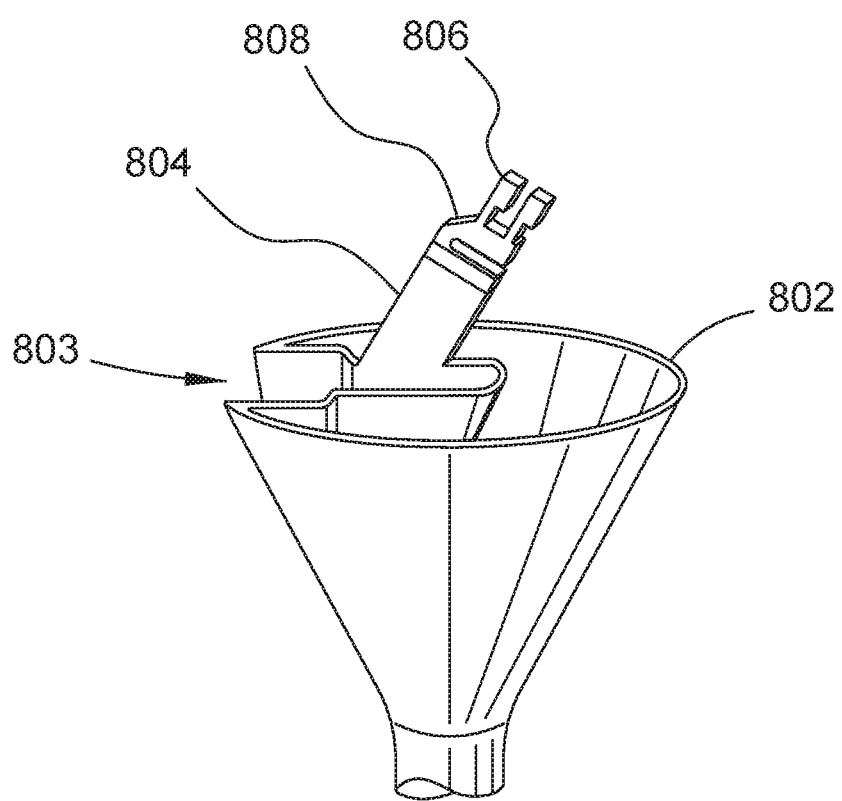
FIG. 8 is a perspective view of the top portion of a collection vessel having an integral wire lock, in accordance with some embodiments.

FIG. 8 is a perspective view of the top portion of a collection vessel 800 having an integral wire lock, in accordance with some embodiments. The catch portion 802 includes an indented portion 803, substantially as previously described. The indented portion 803 is sized and shaped to receive the neck and a section of the main body of the endoscope, and to position the portion substantially in the center of the opening at the top of the catch portion 802. As shown in FIGS. 3-4, the port 308 is oriented at an angle to the main endoscope body. As also mentioned, it is common for a physician to insert a guide wire into the port, down the endoscope channel, into, for example, a bile duct in a patient. To prevent the wire from shifting relative to the endoscope, a wire lock is commonly used. Here, and wire lock 806 is provided on the top of an extension 804 that extends up from the top of the wall of the catch portion 802 that defines one of the inner wall sections of the indented portion 803. The wire lock 806 has features in which a guide wire can be frictionally retained by mechanical interference. That is, the material of the wire lock 806 can be deflected by the guide wire, creating a force against the guide wire that tends to hold the guide wire in place. A clip portion 808 can further restrain a guide wire during use.

Figure 9:
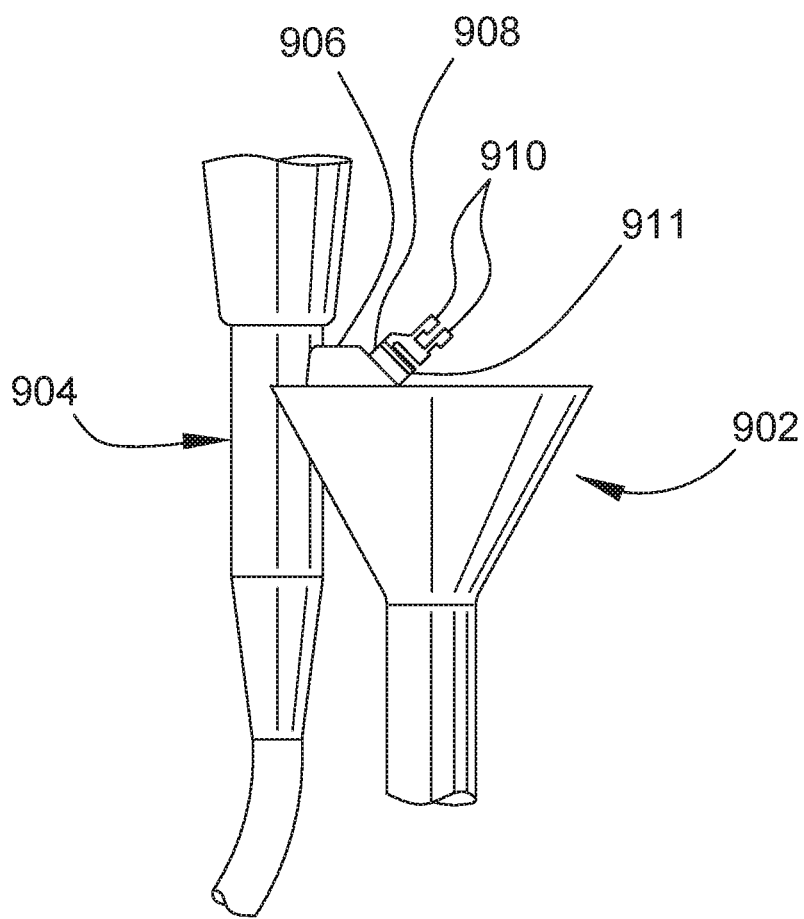
FIG. 9 is a side view of a collection vessel having an integral wire lock configured to be adjacent the port of the endoscope, in accordance with some embodiments.

FIG. 9 is a side view 900 of a collection vessel 902 having an integral wire lock 910 configured to be adjacent the port 908 of the endoscope 904, in accordance with some embodiments. In this view the collection vessel 902 is mounted onto, or otherwise coupled to the endoscope 904, and the neck 906 and part of the main body section of the endoscope are in the indented portion of the collection vessel's catch portion. The collection vessel is designed substantially similar to that shown in FIG. 8. and the wire lock 910 is located immediately adjacent the port 908. A lip or ledge 911 under the wire lock 910 can rest on a side portion of the top of the port 908, adjacent the access opening of the port 908. The wire lock 910 can be provided on an extension integrally formed, or otherwise attached to the indented portion, or from another location of the catch portion. The wire lock 910 features a semi-rigid plastic-like material with "V" shaped slots/notches or similar narrowing features which are configured to frictionally hold a guide wire when the guide wire is suitably directed through a narrowed section of the wire lock 910.

Figure 10:
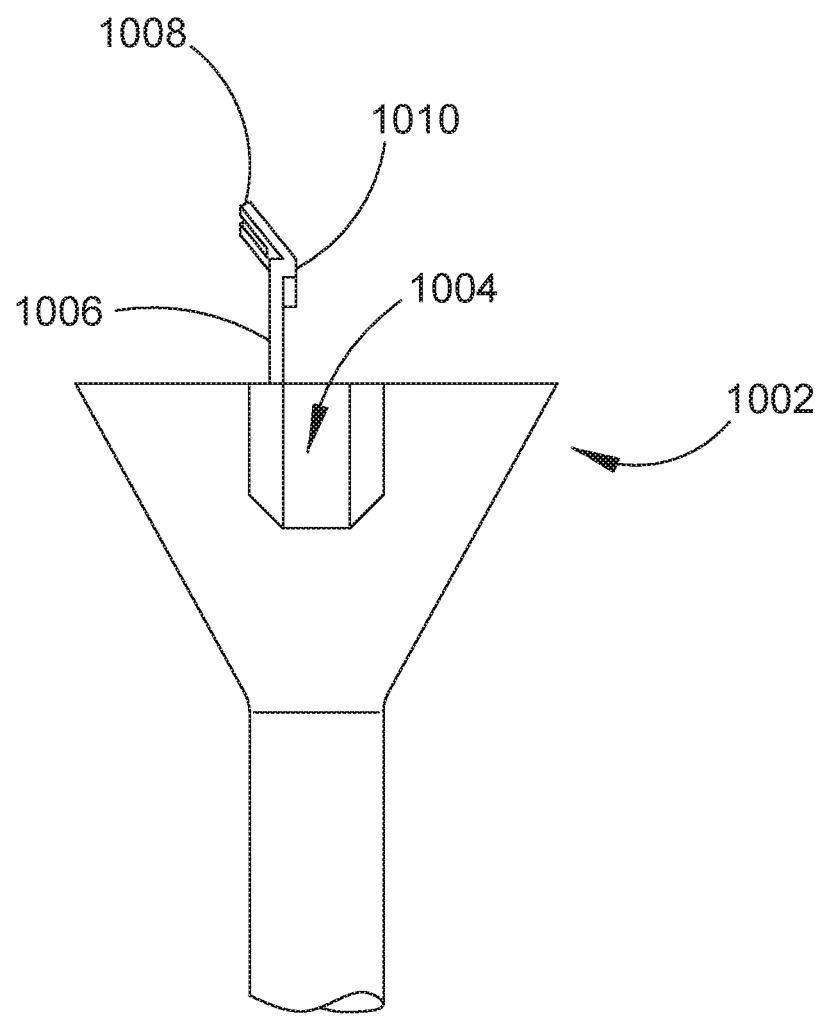
FIG. 10 is a front view of the top portion of a collection vessel having an integral wire lock, in accordance with some embodiments.

FIG. 10 is a front view 1000 of the top portion of a collection vessel 1002 having an integral wire lock, in accordance with some embodiments. The collection vessel includes a catch portion (inverted conic shaped) having an indented portion 1004. From this view the wire lock structure is seen from the side. An extension 1006 can extend upward from a side of the intended portion 1004, and in particular from the rim of the catch portion around the indented portion 1004. At the top of the extension 1006 there can be a lip or ledge 1010 that is configured to sit against, or in close proximity to the top surface of a port of an endoscope. The wire lock 1008 extends further upward, and can be angled away from the port in some embodiments. In some embodiments, the extension 1006 can be formed integrally with the material of the collection vessel 1002 or it can be separate and attached to the collection vessel.

Figure 11:
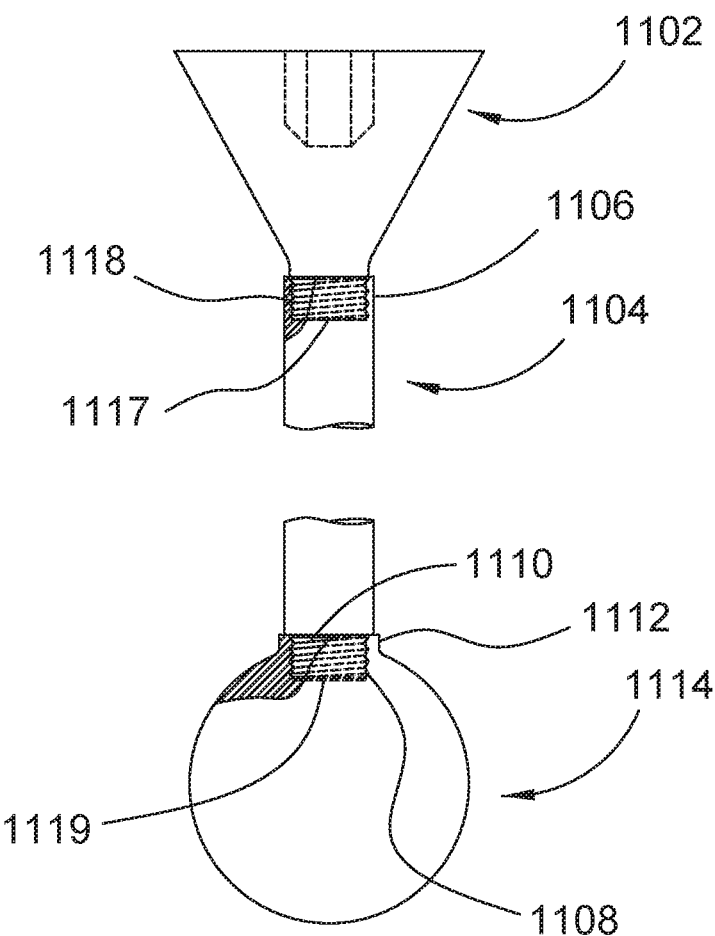
FIG. 11 is side view of a collection vessel cable of being assembled and disassembled, in accordance with some embodiments.

FIG. 11 is side view of a collection vessel 1100 cable of being assembled and disassembled, in accordance with some embodiments. The collection vessel 1100 comprises three major components; the catch portion 1102, the neck portion 1104, and the collection chamber 1114. The three components can be joined together to form the collection vessel 1100, and in some embodiments there can be components of different shapes and dimensions that can be combined to suit a user's preferences or to fit on particular models of endoscopes. For example, the neck portion 1104 can be provided in several different lengths. In some embodiments the components can be threaded together by thread features formed in the material of the components. For example, at a top 1106 of the neck portion 1104, the inside 1118 of the top of the neck portion can be threaded to mate with a threaded extension 1117 at the bottom of the catch portion that threads into the top 1106 of the neck portion 1104. That is the threaded extension 1117 is configured to thread into the top 1106 of the neck portion 1104. By having the upper component (e.g. the catch portion) thread into the lower component (e.g. the neck portion), there is no path through which fluids could seep or leak out. That allows the use of non-sealing threads 1108, which are easier and less costly to form. Likewise, threads 1110 can be formed at a threaded extension 1119 at the bottom of the neck portion 1104 which mate with threads on the inside of a top portion 1112 of the collection chamber 1114. Thus, the neck portion 1104 has the threads 1110 on the outside surface of the threaded extension 1119, and mating threads 1108 are formed on the inside of the top 1106 of the neck portion such that the threaded extension 1119 is configured to thread into the top of the collection chamber 1114. In some embodiments the components can be coupled together using mechanical interference features, such as corresponding ridges, however, at each joint the upper component should fit into the lower component in order to eliminated fluid leakage.

Figure 12:
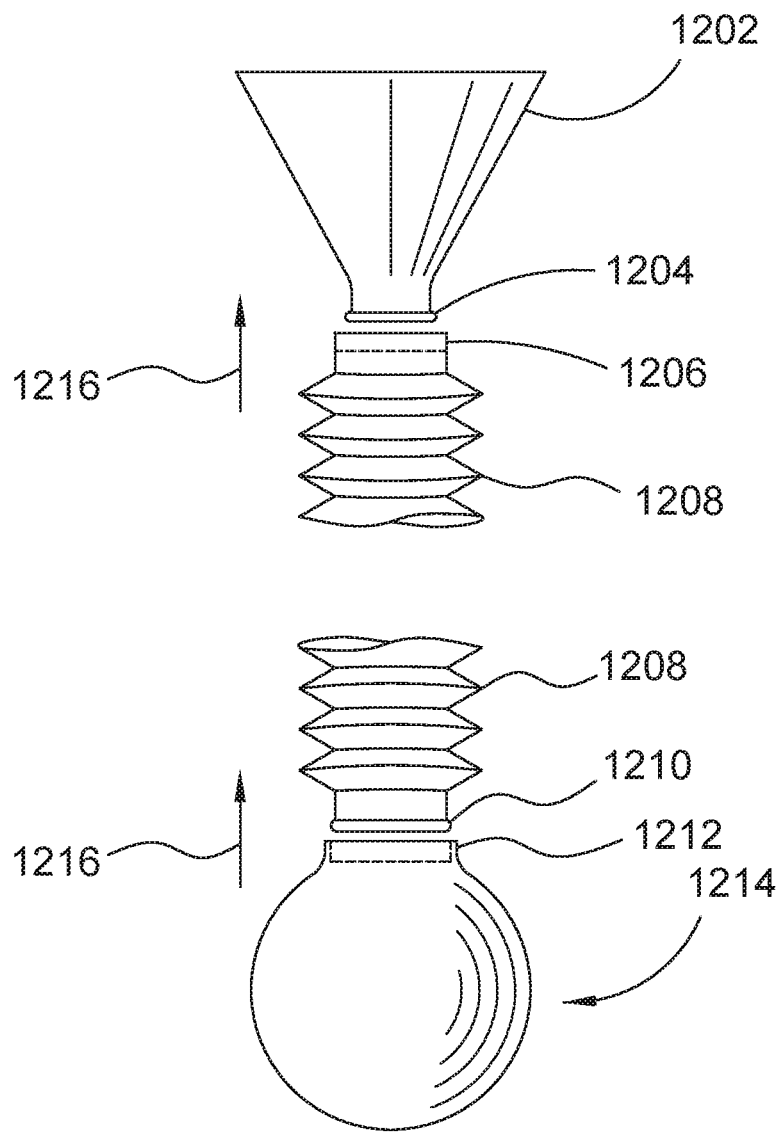
FIG. 12 is a side view of a collection vessel having an accordion configured neck portion for adjusting a length of the neck portion and a position of the collection chamber, in accordance with some embodiments.

FIG. 12 is a side view of a collection vessel 1200 having an accordion configured neck portion 1208 for adjusting a length of the neck portion 1208 and a position of the collection chamber 1214, in accordance with some embodiments. The catch portion 1202 has a lower extension including a peripheral ridge 1204 around the bottom of the extension that fits into the top 1206 of the neck portion 1208 in an interference relationship with a similar ridge formed on the inside of the top 1206 of the neck portion 1208. The neck portion is flexible or bendable by having at least a portion of the neck portion 1208 being formed of accordion sections that can collapse or expand the neck portion 1208 lengthwise, as indicated by arrows 1216. An accordion section comprises two portions that are joined together along a fold and that can be collapsed or folded together in a bellows arrangement, where they are adjacent or against each other, or expanded where they angle away from each other from the fold line where they are joined in the folding bellows arrangement.

Figure 13:
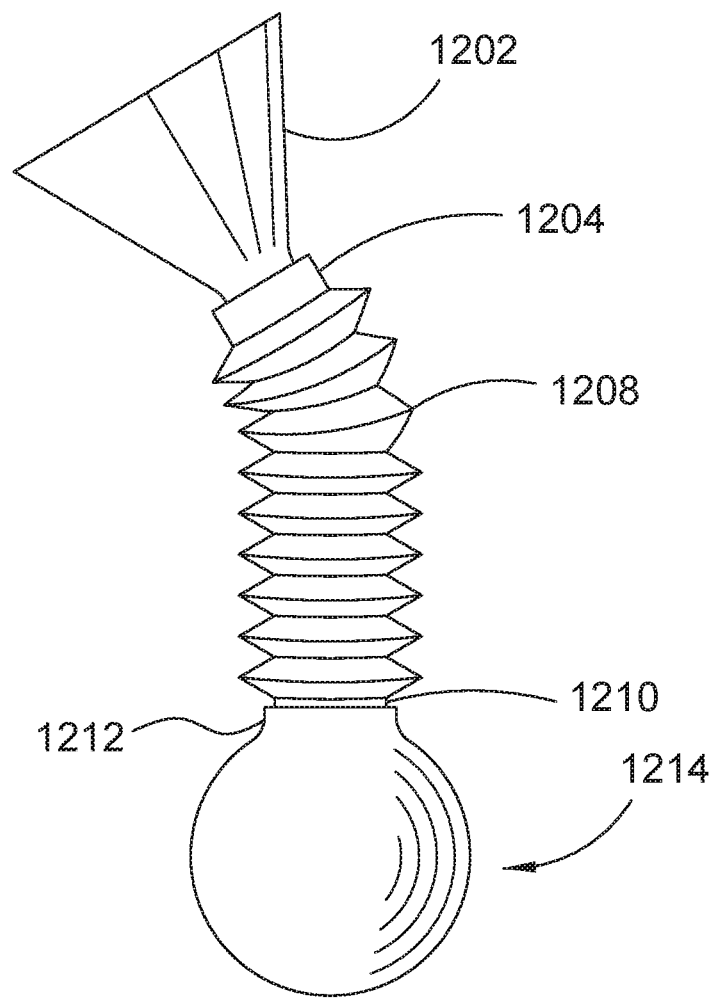
FIG. 13 is a side view of a collection vessel having an accordion configured neck portion for adjusting a length of the neck portion and a position of the collection chamber, in accordance with some embodiments.

At the bottom of the neck portion is an extension having a ridge 1210 around the outside periphery that is used to couple to the top 1212 of the collection chamber 1214 in an interference relationship with a corresponding ridge formed inside the top 1212 of the collection chamber. As illustrated in FIG. 13, the accordion type neck portion 1208 allows the neck portion 1208 to bend by collapsing some of the accordion features on one side, in the vertical direction, and expanding the same according features on the opposite side of the neck portion 1208.

A collection vessel has been disclosed that is configured to be used with an endoscope to catch and collect bodily fluids that may leak out of the port of the endoscope during use. The collection vessel provides the benefit of capturing the fluids away from the controls of the endoscope and reducing the likelihood of inadvertent spillage should, for example, the endoscope/collection vessel be bumped, or dropped during usage. Furthermore, in some embodiments, the collection vessel can be configured to a user preference by providing the various major sections of the collection vessel as individual components that can be joined together. Individual components can then be provided in various dimensions and with various features to suit user preference.

What is claimed is:

1. A collection vessel for use with an endoscope, the endoscope having a main body portion having a neck extending from the main body portion, and a port at a top of the neck, the collection vessel comprising:
   a catch portion configured to be positioned under the neck of the endoscope, the catch portion having an open top defined by a rim, and a wall extending downward and inward from the rim to a bottom opening of the catch portion, an indented portion formed in the wall at a top of the wall wherein a portion of the wall and the rim deviate inward forming a wide section and a sloping portion, the wide section is defined by opposing outer wall sections that extend inward from an outer circumference of the catch portion, parallel to each other, to respective shoulder portions, the shoulder portions extend toward each other from the respective outer wall sections each to a respective inner wall section, the inner wall sections extend inward from the shoulder portions to a back section of the sloping portion, the back section of the sloping portion slopes outward from a top of the back section to a bottom of the sloping portion at the shoulder portions, and wherein a distance between the outer wall sections is greater than a distance between the inner wall sections;
   a neck portion joined at a top of the neck portion to the bottom of the catch portion at the bottom opening of the catch portion, the neck extending downward from the bottom of the catch portion and having a bore through the neck portion to a bottom of the neck portion; and
   a collection chamber joined to the bottom of the neck portion defining a collection volume within a wall of the collection chamber, wherein the wall of the collection chamber extends outward from the bottom of the neck portion.

2. The collection vessel of claim 1, wherein the catch portion is conically shaped.

3. The collection vessel of claim 1, wherein a wire lock portion extends upward from one of the inner wall sections of the indented portion and is configured to be adjacent the port at the top of the neck of the endoscope.

4. The collection vessel of claim 1, wherein the neck portion is cylindrical, having circular cross section.

5. The collection vessel of claim 1, wherein the neck portion further includes, in the bore of the neck portion, at least one downward angled backflow prevention wall that extends from one side of the bore across a central axis of the bore to a free end of the at least one downward angled backflow prevention wall, and wherein there is a gap between the free end and an opposite side of the bore.

6. The collection vessel of claim 5, wherein the at least one downward angled backflow prevention wall is a first downward angled backflow prevention wall, the neck portion further includes a second downward angled backflow prevention wall below the first downward angled backflow prevention wall, wherein the second downward angled backflow prevention wall is oriented in an opposite direction from that of the first downward angled backflow prevention wall.

7. A collection vessel for use with an endoscope, the endoscope having a main body portion, the main body portion of the endoscope having a neck extending from the main body portion, and a port at a top of the neck, the collection vessel comprising:
   a catch portion having an inverted conic shape that is open at a top of the catch portion and that defines a rim that is substantially circular, the catch portion further including a wall extending downward and inward from the rim to a bottom of the catch portion which includes a bottom opening, and an indented portion formed in the wall from the rim that is shaped to correspond to the neck of the endoscope and wherein the indented portion is shaped such that when the indented portion is positioned over the neck of the endoscope, the port on the neck of the endoscope is substantially centered over the top of the catch portion;
   a neck portion joined at a top of the neck portion to the bottom of the catch portion at the bottom opening of the catch portion, the neck extending downward from the bottom of the catch portion and having a bore through the neck portion to a bottom of the neck portion;
   a collection chamber joined to the bottom of the neck portion defining a collection volume within a wall of the collection chamber, wherein the wall of the collection chamber extends outward from the bottom of the neck portion; and
   the neck portion further including at least one backflow prevention feature disposed in the bore of the neck portion that is configured to inhibit a flow of fluid toward the catch portion and to facilitate flow of fluid in a direction toward the collection chamber.

8. The collection vessel of claim 7, wherein a wire lock portion extends upward from a side of the indented portion and is configured to be adjacent the port at the top of the neck of the endoscope.

9. The collection vessel of claim 7, wherein the neck portion is cylindrical, having circular cross section.

10. The collection vessel of claim 7, wherein the at least one backflow prevention feature includes at least one downward angled backflow prevention wall that extends from one side of the bore across a central axis of the bore to a free end of the at least one downward angled backflow prevention wall, and wherein there is a gap between the free end and an opposite side of the bore.

11. The collection vessel of claim 10, wherein the at least one downward angled backflow prevention wall is a first downward angled backflow prevention wall, the neck portion further includes a second downward angled backflow prevention wall below the first downward angled backflow prevention wall, wherein the second downward angled backflow prevention wall is oriented in an opposite direction from that of the first downward angled backflow prevention wall.

* * * * *